(12) United States Patent
Schmidt et al.

(10) Patent No.: US 6,846,679 B1
(45) Date of Patent: Jan. 25, 2005

(54) CHARACTERIZING POLYPEPTIDES THROUGH CLEAVAGE AND MASS SPECTROMETRY

(75) Inventors: Gunter Schmidt, Houghton (GB); Andrew Hugin Thompson, Alloway (GB)

(73) Assignee: Xzillion GmbH & Co., KG, Frankfurt am Main (DE)

( * ) Notice: Subject to any disclaimer, the term of this patent is extended or adjusted under 35 U.S.C. 154(b) by 0 days.

(21) Appl. No.: 09/806,564

(22) PCT Filed: Oct. 1, 1999

(86) PCT No.: PCT/GB99/03258

§ 371 (c)(1), (2), (4) Date: Jul. 19, 2001

(87) PCT Pub. No.: WO00/20870

PCT Pub. Date: Apr. 13, 2000

(51) Int. Cl.[7] ............................................. G01N 33/50
(52) U.S. Cl. ......................... 436/89; 436/86; 436/173; 435/23; 435/24
(58) Field of Search ........................... 436/89, 86, 173; 435/23, 24

(56) References Cited

U.S. PATENT DOCUMENTS

| | | | | |
|---|---|---|---|---|
| 5,431,882 A | * | 7/1995 | Nokihara et al. | 422/62 |
| 5,470,703 A | * | 11/1995 | Nokihara et al. | 435/4 |
| 5,792,664 A | * | 8/1998 | Chait et al. | 436/89 |
| 5,824,556 A | * | 10/1998 | Tarr | 436/89 |
| 5,827,659 A | * | 10/1998 | Patterson | 435/6 |
| 5,869,240 A | * | 2/1999 | Patterson | 435/6 |
| 6,124,137 A | * | 9/2000 | Hutchens et al. | 436/155 |
| 6,245,331 B1 | * | 6/2001 | Laal et al. | 424/168.1 |
| 6,271,037 B1 | * | 8/2001 | Chait et al. | 436/89 |
| 6,379,971 B1 | * | 4/2002 | Schneider et al. | 436/89 |
| 6,489,121 B1 | * | 12/2002 | Skilling | 435/7.1 |

FOREIGN PATENT DOCUMENTS

| | | |
|---|---|---|
| GB | 2168478 A | 6/1986 |
| WO | WO 95/25281 | 9/1995 |
| WO | WO 96/36986 | 11/1996 |
| WO | WO 98/32876 | 7/1998 |

OTHER PUBLICATIONS

Gudrun Bennett et al.: "Identification of Ser–Pro and Thr–Pro Phosphorylation Sites in Chicken Neurofilament–M Tail Domain", J. Neurochem. 68(2): 534–543 (1997).

Damon I. Papac et al.: "Palmitylation of a G–Protein Coupled Receptor. Direct Analysis by Tandem Mass Spectrometry", J. Biol. Chem. 267(24): 16889–16894 (1992).

Mami Furuya et al.: "The Primary Structure of Human EGF Produced by Genetic Engineering, Studied by High–Performance Tandem Mass Spectrometry", Biochem. Biophys. Res. Commun. 163(2): 1101–1106 (1989).

Yiping Sun et al.: "Identification of the Active Site Serine of Penicillin–Binding Protein 2a from Methicillin–Resistant *Staphylococcus aureus* by Electrospray Mass Spectrometry", J. Mass Spectrom. 33(10): 1009–1016 (1998).

Chantal Korostensky et al.: "An algorithm for the Identification of Proteins Using Peptides with Ragged N– or C–Termini Generated by Sequential Endo– and Exopeptidase Digestions", Electrophoresis 19(11): 1993–1940 (1998).

* cited by examiner

*Primary Examiner*—Jon P. Weber
*Assistant Examiner*—David Lukton
(74) *Attorney, Agent, or Firm*—Pillsbury Winthrop LLP

(57) ABSTRACT

Provided is a method for characterizing a polypeptide or a population of polypeptides, which method comprises: (a) contacting a sample comprising one or more polypeptides with a first cleavage agent to generate polypeptide fragments; (b) isolating one or more polypeptide fragments, each fragment comprising the N-terminus or the C-terminus of the polypeptide from which it was fragmented; (c) identifying the isolated fragments by mass spectrometry; (d) repeating steps (a)–(c) on the sample using a second cleavage agent that cleaves at a difference site from the first cleavage agent; and (e) characterizing the one or more polypeptides in the sample from the fragments identified in steps (c) and (d).

20 Claims, No Drawings

CHARACTERIZING POLYPEPTIDES THROUGH CLEAVAGE AND MASS SPECTROMETRY

This application is a 371 of PCT/GB99/03258 filed Oct. 1, 1999, which claims priority to UK application 9821393-7, filed Oct. 1, 1998.

This invention relates to a method for characterising polypeptides using mass spectrometry to identify the terminal fragments of the polypeptides. The method involves cleaving the polypeptides and isolating a single terminal peptide from each protein in a population. This invention further relates to the use of the above methods in methods of determining the expression of proteins in a tissue, cell type, or sub-cellular compartment or in analysing large protein complexes.

Techniques for profiling proteins, that is to say cataloguing the identities and quantities of proteins in a tissue, are not well developed in terms of automation or high throughput. The classical method of profiling a population of proteins is by two-dimensional electrophoresis (R. A. Van Bogelen., E. R, Olson, "Application of two-dimensional protein gels in biotechnology.", Biotechnol. Annu. Rev., 1:69–103, 1995). In this method a protein sample extracted from a biological sample is separated on a narrow gel strip. This first separation usually separates proteins on the basis of their isoelectric point. The entire gel strip is then laid against one edge of a rectangular gel. The separated proteins in the strip are then electrophoretically separated in the second gel on the basis of their size. This technology is slow and very difficult to automate. It is also relatively insensitive in its simplest incarnations.

A number of improvements have been made to increase resolution of proteins by 2-D gel electrophoresis and to improve the sensitivity of the system. One method to improve the sensitivity of 2-D gel electrophoresis and its resolution is to analyse the protein in specific spots on the gel by mass spectrometry (Jungblut P. Thiede B. "Protein identification from 2-DE gels by MALDI mass spectrometry." Mass Spectrom. Rev. 16:145–162, 1997). One such method is in-gel tryptic digestion followed by analysis of the tryptic fragments by mass spectrometry to generate a peptide mass fingerprint. If sequence information is required, tandem mass spectrometry analysis can be performed.

More recently attempts have been made to exploit mass spectrometry to analyse whole proteins that have been fractionated by liquid chromatography or capillary electrophoresis (Dolnik V. "Capillary zone electrophoresis of proteins.", Electrophoresis 18, pp 2353–2361, 1997). In-line systems exploiting capillary electrophoresis mass spectrometry have been tested. The analysis of whole proteins by mass spectrometry, however, suffers from a number of difficulties. The first difficulty is the analysis of the complex mass spectra resulting from multiple ionisation states accessible by individual proteins. The second major disadvantage is that the mass resolution of mass spectrometers is at present quite poor for high molecular weight species, i.e. for ions that are greater than about 4 kilodaltons in mass. Thus, resolving proteins that are close in mass is difficult. A third disadvantage is that further analysis of whole proteins by tandem mass spectrometry is difficult as the fragmentation patterns for whole proteins are extremely complex and difficult to interpret.

WO 98/32876 discloses methods for profiling a population of proteins by isolating a single peptide from each protein in the population. The method disclosed in this application comprises the following steps:

1. Capturing a population of proteins onto a solid phase support by one terminus of each protein in the population.
2. Cleaving the captured proteins with a sequence specific cleavage agent.
3. Washing away peptides generated by the cleavage agent not retained on the solid phase support.
4. Releasing the terminal peptides retained on the solid phase support.
5. Analysing the released terminal peptides preferably identifying and quantifying each peptide in the mixture. The analysis is preferably performed by mass spectrometry.

In this application, the C-terminus is indicated to be more preferable as the terminus by which to capture a population of proteins, since the N-terminus is often blocked. In order to capture a population of proteins by the C-terminus, the C-terminal carboxyl group must be distinguished from other reactive groups on a protein and must be reacted specifically with a reagent that can effect immobilisation. In many C-terminal sequencing chemistries the C-terminal carboxyl group is activated to promote formation of an oxazolone group at the C-terminus. During the activation of the C-terminal carboxyl, side chain carboxyls are also activated but these cannot form an oxazolone group. It has been reported that the C-terminal oxazolone is less reactive to nucleophiles under basic conditions than the activated side-chain carboxyls, offering a method of selectively capping the side chain carboxyl groups (V. L. Boyd et al., Methods in Protein Structure Analysis: 109–118, Plenum Press, Edited M. Z. Atassi and E. Appella, 1995). Other more reactive side chains can be capped prior to the activation of the carboxyls using a variety of conventional reagents. In this way all reactive side chains can be capped and the C-terminus can be specifically labelled.

EP-A-0 594 164 describes a method of isolating a C-terminal peptide from a protein in a method to allow sequencing of the C-terminal peptide using N-terminal sequencing reagents. In this method the protein of interest is digested with an endoprotease which cleaves at the C-terminal side of lysine residues. The resultant peptides are reacted with DITC polystyrene which reacts with all free amino groups. N-terminal amino groups that have reacted with the DITC polystyrene can be cleaved with trifluoroacetic acid (TFA) thus releasing the N-terminus of all peptides. The epsilon amino group of lysine is not cleaved, however, and all non-terminal peptide are thus retained on the support and only C-terminal peptides are released. According to this patent the C-terminal peptides are recovered for micro-sequencing.

However, none of the above methods is capable of readily identifying all of the proteins present in a population, and in fact many of these methods cannot uniquely identify all of the proteins present at all.

Accordingly, it is an object of the present invention to overcome the problems associated with the prior art, and to provide a method for characterising polypeptides which is capable of uniquely identifying a greater proportion of proteins present in a sample, than is possible using prior art methods. It is thus an object of the present invention to provide improved methods for isolating a single terminal peptide from each protein in a mixture, complex or population (prepared in an arbitrary fashion). A further object of this invention is to provide such methods that are amenable to automation. It is also an object of this invention to provide methods to improve the sensitivity of the mass spectrometry analysis of terminal peptides generated by the methods of this invention.

Accordingly the present invention provides a method for characterising a polypeptide or a population of polypeptides, which method comprises:

(a) contacting a sample comprising one or more polypeptides with a first cleavage agent to generate polypeptide fragments;

(b) isolating one or more polypeptide fragments, each fragment comprising the N-terminus or the C-terminus of the polypeptide from which it was fragmented;

(c) identifying the isolated fragments by mass spectrometry;

(d) repeating steps (a)–(c) on the sample using a second cleavage agent that cleaves at a different site from the first cleavage agent; and (e) characterising the one or more polypeptides in the sample from the fragments identified in steps (c) and (d).

In the context of the present invention a polypeptide includes any peptide comprising two or more amino acids, and includes any protein. In the present context, the sample used in the repeat step (d) is the same sample as that used in step (a). The "same sample" may mean (for example) one of a plurality of portions separated from one original sample, there being one portion for each repetition of the steps (a)–(c).

The steps (a)–(c) can be repeated any number of times, e.g. once, twice or more times. For each repetition a cleavage agent is used which cleaves at a different site than the previous cleavage agents used. This gives a different set of terminal fragments for each repetition, even though the same sample is being treated. If two or more proteins cannot be distinguished by means of their terminal fragments produced by cleavage at a particular site (e.g. if two or more proteins have terminal fragments sharing the same or indistinguishable mass) then cleavage at a different site may (for the same two or more proteins) produce terminal fragments of different masses. Thus the resolution of the method is enhanced by repetition using a plurality of different cleavage agents.

The cleavage agents used in the present invention are not especially limited. Preferred cleavage agents include an endopeptidase or a chemical cleavage agent. More preferably the cleavage agent employed comprises Lys-C endopeptidase, a thiocyanate compound, cyanogen bromide, BNPS-skatole, trypsin, chymotrypsin, and/or thrombin.

The present invention also provides a method for characterising a polypeptide or a population of polypeptides, which method comprises:

(f) contacting a sample comprising one or more polypeptides with a first capping agent in a first capping step to introduce capping groups on one or more reactive side chains of the polypeptides;

(g) contacting the sample with a cleavage agent to generate polypeptide fragments;

(h) isolating one or more polypeptide fragments, each fragment comprising the N-terminus or the C-terminus of the polypeptide from which it was fragmented;

(j) identifying the isolated fragments by mass spectrometry;

(k) repeating steps (f)–(j) on the sample using a second capping agent that introduces capping groups at the same side chains as the first capping step, but uses capping groups having different mass than the capping groups used in the first capping step; and (l) characterising the one or more polypeptides in the sample from the fragments identified in steps (j) and (k).

The method may use the same cleavage agent or different cleavage agents for each repetition, as long as capping groups having different masses are employed; for each repetition. The steps (f)–(j) can be repeated any number of times, e.g. once, twice or more times. For each repetition a capping group is used which has a different mass than the corresponding previous capping group that was used. This gives a different set of terminal fragments for each repetition, even though the same sample is being treated with the same cleavage agent. If two or more proteins cannot be distinguished from their terminal fragments capped with a particular capping group or groups (e.g. if two or more proteins have terminal fragments sharing the same or indistinguishable mass) then use of one or more capping groups having a different mass to the corresponding groups used in the previous capping step may (for the same two or more proteins) produce terminal fragments of different masses. Thus the resolution of the method is enhanced by repetition using a plurality of capping groups, each having a different mass.

In the above-described methods, when the side chains of the proteins in the population are to be capped, the side chains to be capped may comprise one or more of the following:

the $NH_2$ side chain in arginine;

the $NH_2$ side chain in asparagine;

the $NH_2$ side chain in glutamine;

the $NH_2$ side chain in lysine;

the COOH side chain in aspartic acid;

the COOH side chain in glutamic acid;

the OH side chain in serine;

the OH side chain in threonine;

the OH side chain in thyroxine;

the OH side chain in tyrosine; and the SH side chain in cysteine.

The capping agents used in the present invention are not especially limited. Preferred capping agents include iodoacetate compounds, isocyanate compounds (e.g. phenyl isocyanate), silyl compounds (e.g. trimethylchlorosilane), anhydride compounds (e.g. acetic anhydride and trimethylacetic anhydride), vinylsulphone compounds (e.g. phenyl vinylsulphone and methyl vinylsulphone) and vinyl pyridine derivatives (e.g. 4-vinyl pyridine). The mass of the capping group can be altered by substitution. Such substitution is not particularly limited, provided that the capping reaction is still able to proceed. Substitution with deuterium or a halogen such as an iodine group is preferred.

Thus, in one preferred aspect, this invention provides a method of generating a protein expression profile with improved resolution by combining two or more protein expression profiles where the profiles have been generated from the same protein mixture but which have been treated with two or more different sequence specific cleavage agents. A different sequence specific cleavage agent being used in the generation of each individual profile. In this context resolution refers to the proportion of proteins in a population that can be identified uniquely from a database on the basis of their terminal peptide mass alone.

In a further preferred aspect this invention provides a method of generating a protein expression profile with improved resolution by combining two or more expression profiles where the profiles have been generated from the same protein mixture and have been cleaved with the same sequence specific cleavage reagent but where specific side chains, such as amino acid side chains, have been capped with two or more capping reagents with different masses. A different set of capping agents is used in the generation of each individual profile.

More preferred aspects of the invention will now be discussed in detail. In a first preferred aspect, this invention provides a method of generating a population of terminal peptides comprising the steps of:

1. Immobilising a population of proteins onto a solid support.
2. Contacting the immobilised population of proteins with a reagent which reacts with the alpha-amino group at the N-terminus of the proteins and with any lysine epsilon-amino groups. This reagent may optionally also react with any serine and threonine side chains in order to cap them. In this context capping means reacting the side-chains with a reagent which will render the side-chains unreactive to any other reagents used in the subsequent steps of this method. If the reagent does not cap side chains other than amine groups additional capping agents may be applied to cap other reactive side chains so that substantially all reactive side-chains are capped.
3. Contacting the protein population with a reagent that will 'activate' the free carboxyl groups of the proteins. The activation reagent should preferably promote the formation of an oxazolone group at the C-terminal activated carboxyls of the proteins in the population.
4. Contacting the resultant derivitised proteins with a nucleophile under basic conditions to cap the activated side chain carboxyl derivatives. The C-terminal oxazolinone is less reactive to nucleophiles than the activated side chain carboxyls. In this way all reactive side chain functionalities are capped. Preferably the nucleophile is added as a thiocyanate salt.
5. Contacting the reaction mixture with an appropriate acid, preferably TFA, which promotes reaction of the C-terminal oxazolone group with thiocyanate to give a C-terminal thiohydantoin derivative.
6. Contacting the proteins with a cleavage agent to cleave the C-terminal thiohydantoin from the derivitised proteins to expose the carboxyl of the penultimate amino acid in each protein.
7. Contacting the exposed penultimate carboxyl with an appropriate reagent to permit solid phase capture of proteins by the C-terminus.
8. Contacting the C-terminally modified proteins with a sequence specific cleavage agent.
9. Capturing the C-terminal peptides onto a solid phase support and washing away the non-terminal peptides.
10. Optionally reacting the terminal amine group of the captured peptides with a mass spectrometry sensitisation reagent.
11. Releasing the captured C-terminal peptides from the solid phase support.
12. Recovering the released peptides.
13. Analysing the C-terminal peptides by mass spectrometry.

Any one of the above preferred steps, or any combination of the above preferred steps can be utlised in the general methods of the invention as already described above.

In a second preferred aspect this invention provides a method of generating a population of terminal peptides comprising the steps of:

1. Immobilising a population of proteins onto a solid phase support.
2. Contacting the immobilised population of proteins with a reagent which reacts with the alpha-amino group at the N-terminus of the proteins and with any lysine epsilon-amino groups. This reagent may optionally also react with any serene and threonine side chains in order to cap them. In this context capping means reacting the side-chains with a reagent which will render the side-chains unreactive to any other reagents used in the subsequent steps of this method. If the reagent does not cap side chains other than amine groups additional capping agents may be applied to cap other reactive side chains so that substantially all reactive side-chains are capped.
3. Contacting the protein population with a reagent that will 'activate' the free carboxyl groups of the proteins. The activation reagent should preferably promote the formation of an oxazolone group at the C-terminal activated carboxyls of the proteins in the population.
4. Contacting the resultant derivitised proteins with a nucleophile under basic conditions to cap the activated side chain carboxyl derivatives. The C-terminal oxazolinone is less reactive to nucleophiles than the activated side chain carboxyls. In this way all reactive side chain functionalities are capped. Preferably the nucleophile is added as a salt with an inert anion.
5. Hydrolysing, the C-terminal oxazolone to regenerate the C-terminal carboxyl species.,
6. Contacting the proteins with an activation agent to activate the C-terminal carboxyl group
7. Contacting the activated terminal carboxyl group with an appropriate reagent to permit solid phase capture of proteins by the C-terminus.
8. Contacting the C-terminally modified proteins with a sequence specific cleavage agent.
9. Capturing the C-terminal peptides onto a solid phase support and washing away the non-terminal peptides.
10. Optionally reacting the terminal amine group of the captured peptides with a mass spectrometry sensitisation reagent.
11. Releasing the captured C-terminal peptides from the solid phase support.
12. Recovering the released peptides.
13. Analysing the C-terminal peptides by mass spectrometry.

Any one of the above preferred steps, or any combination of the above preferred steps can be utilised in the general methods of the invention as already described above.

In a third preferred aspect, this invention provides a method of generating a population of terminal peptides from a population of proteins comprising the steps of:

1. Digesting a population of proteins completely with a Lys-C specific cleavage enzyme, i.e. a reagent that cuts at the peptide bond immediately agent to a lysine residue on the C-terminal side of that residue.
2. Contacting the resultant peptides with an activated solid support that will react with free amino groups.
3. Contacting the captured peptides with a reagent that which cleaves at the alpha amino groups of each peptide on the support. All peptides that are not C-terminal will have a lysine residue covalently linking them to the solid support. Thus free C-terminal peptides are selectively released.
4. Recovering the released peptides.
5. Optionally contacting the released peptide with reagents to cap reactive side chains.

6. Optionally reacting the terminal amine group of the captured peptides with a mass spectrometry sensitisation reagent.

7. Analysing the peptides by mass spectrometry.

Any one of the above preferred steps, or any combination of the above preferred steps can be utilised in the general methods of the invention as already described above.

In order that only the fragments containing lysine residues remain bound to the solid support via two amino groups, (so that all fragments except those containing lysine groups are released from the solid support during the releasing step) the fragments are preferably attached to the solid phase at a pH at which the side chain $NH_2$ of lysine is not protonated. Thus, this step is preferably carried out at a pH of from 11–11.5.

Generation of a population of C-terminal peptides

The use of C-terminal sequencing reagents

Various preferred embodiments of the above aspects of this invention are discussed below.

In the first step of the first and second preferred aspects of this invention, a population of proteins is immobilised onto a solid phase support, preferably non-covalently. Zitex (porous Teflon from Norton Performance Plastics, Wayne, N.J.) membranes can be used to effect non-covalent immobilisation of proteins on a solid phase support (Bailey et al., "Automated carboxy-terminal sequence analysis of peptides and proteins using diphenyl phosphoroisothio-cyanatidate", Protein Science 1:1622–1633, 1992; Bailey et al., Anal. Biochem. 212:366374, 1993.) Polyvinylidenedifluoride membranes (Millipore) can also be used to immobilise proteins.

Step 2 of the first and second preferred aspects of this invention involves capping of the reactive side chains of a population of proteins. It is well known in the art that the reactive side-chain functionalities can be selectively capped. Reactive side-chains include lysine, serine, threonine, tyrosine and cysteine. Cysteine is often cross-linked with itself to form disulphide bridges. For the purposes of this invention it is preferred that these bridges are broken. This can be effected by reducing the disulphide bridge to a pair of thiols with mercaptethanol. Thiols can be selectively capped by iodacetate (Aldrich) under mildly basic conditions which promote the formation of a thiolate ion (Mol. Microbiol 5:2293, 1991). An appropriate mild base would be a carbonate. In other embodiments the population of proteins may be treated with an isocyanate compound. Isocyanates will react almost exclusively with the alpha-amino group at the N-terminus of the proteins and with any lysine epsilon-amino groups, i.e. with primary amines under mild conditions, i.e. at room temperature in a neutral solvent to give a urea derivative. These reagents cart also be made to react with any hydroxyl bearing side-chains, such as serine, threonine and tyrosine side chains, in the presence of an appropriate catalyst such as pyridine or a tin compound, such as dibutylstanyl laurate, to give a urethane derivative. In an alternative embodiment the population of proteins can be treated with a silyl compound such as trimethylchlorosilane (Sigma). These compounds react readily with most reactive functional groups. Amine derivatives are not stable under aqueous conditions and so can be hydrolysed back to the free amine if that is desired. The above examples are intended to illustrate methods of capping reactive side-chain functionalities and are not intended to limit the scope of this invention. A wide variety of protective groups are known in the art an it is envisaged that a large proportion of these could be used to complete the steps of this invention.

In step 3 of the first and second preferred aspects of this invention the carboxyl side chains are then 'activated'. Acetic anhydride has been widely used for this purpose, which generates mixed anhydrides at carboxyl groups. In some embodiments, step 2 of first and second preferred aspects of this invention may be combined with step 3. Activation of side chain carboxyls with an anhydride compound also results in capping of reactive side chains, such as lysine, serine, threonine and tyrosine. In embodiments where step 2 and 3 are combined, it is preferred that the activation reagent chosen is stable as a capping agent for the reactive side chains, as some anhydride derivatives are not stable under basic or acidic conditions. Trimethylacetic anhydride is more stable under these conditions through steric effects, for example. An alternative, more preferred, activation reagent is Woodwards Reagent K (N-Ethyl-5-phenylisoxazolium-3-sulphonate available from Sigma). In another preferred embodiment of this aspect of the invention, activation is achieved by treatment with a reactive phosphate such as tetraphenyl pyrophosphate (Aldrich) or diphenyl phosphochloridate. According to U.S. Pat. No. 5,665,603, the activation step required in peptide sequencing methods to generate a carboxyl derivative at the C-terminus of a peptide or poly-peptide which can react to form a thiohydantoin can be effected more efficiently under milder conditions with acyl phosphate compounds, such as diphenyl phosphochloridate or tetraphenyl pyrophosphate (Aldrich). The C-terminal carboxyl is reacted with the reactive phosphate in the presence of a base to deprotonate the carboxyl group. Preferred bases are tri-ethylamine, diisopropylethylamine or pyridines, i.e. a base which won't react with the resultant acyl phosphates. The phosphorylation reaction to activate the C-terminal carboxyl preferably uses equimolar quantities of reactive phosphate and base. These two reagents are added in large excess to a poly-peptide in a polar, aprotic solvent, e.g. acetonitrile (ACN), dimethylformamide or an ether, preferably ACN. The reaction is typically complete in 5 to 10 minutes and usually less than 30 minutes at room temperature. Temperature can vary: the reactions are performed at 55° C. in an automated sequencer in line with other reactions taking place. The C-terminal activated derivatives of carboxyl groups will spontaneously cyclise to form an oxazolone intermediate whilst the side chain carboxyls remain activated.

The activated side-chain carboxyl derivatives apparently react with nucleophiles under basic conditions whilst the C-terminal oxazolone group is much less reactive to nucleophiles V. L. Boyd et al., Methods in Protein Structure Analysis: 109–118, Plenum Press, Edited M. Z. Atassi and E. Appella, 1995). Hence, in step four of the first and second preferred aspects of this invention the protein population is contacted with a nucleophile under basic conditions. A preferred nucleophile is a primary amine compound. If amine nucleophiles are used the side chains can be amidated. Preferred amine nucleophiles are piperidine, methylamine, ethylamine or other amine, added with an appropriate base. To perform the amidation reaction equimolar quantities of base and nucleophile are added in a polar aprotic solvent, preferably acetonitrile, with the reagents in a large excess over the mixture of proteins. Ammonia generates asparagine from activated aspartic acid residues and glutamine from glutamic acid residues. This may reduce the information in the peptide's mass and ammonia may not be a preferred nucleophile. In an alternative embodiment an alcohol can be used to esterify the activated side-chain carboxyl derivatives under acidic conditions. An appropriate alcohol, e.g. methanol, can be added in an appropriate, anhydrous acidic solvent, e.g. TFA.

In the first preferred aspect of this invention the nucleophile may be added as a thiocyanate salt. The oxazolone reacts under acidic conditions with isothiocyanate and so after an initial period under basic conditions to promote amidation the reaction is acidified with trifluoracetic acid to promote C-terminal thiohydantoin formation.

In the second preferred aspect of this invention, the amine nucleophile may be added as a salt with an inert group, e.g. a carbonate. Preferably a volatile salt is used to facilitate removal of unused reagent. In this way the oxazolone can be prevented from reacting so that the oxazolone can be hydrolysed to regenerate a free carboxyl at the C-terminus. In a further embodiment the amine nucleophile can be added as a salt with a biotinylation agent with an appropriate functionality to react with the oxazolone.

In the first aspect of this invention where the nucleophile is added as a thiocyanate salt, the reaction mixture is then acidified with an appropriate acid, preferably TFA which promotes reaction of the C-terminal oxazolone group with thiocyanate to give a C-terminal thiohydantoin derivative. The C-terminal thiohydantoin is then cleaved from the derivitised proteins to expose the carboxyl of the penultimate amino acid in each protein. Cleavage of the thiohydantoin from the C-terminal can be effected by a variety of methods including hydrolysis by acid or base. More preferably cleavage is effected by a reagent such as sodium trimethylsilanolate in an alcoholic solvent (J. M. Bailey et al., Protein Science 1:68–80, 1992).

In step 7 of the first and second preferred aspects of this invention the exposed terminal carboxyl may then be reacted with an appropriate reagent to permit solid phase capture of proteins by the C-terminus. A reagent such as biotinamidocaproyl hydrazide is reactive with free carboxylic acids. A reagent such as 5-(biotimamido) pentylamine can be used allowing capture by avidin. Prior to reaction with this biotinylation reagent, free carboxyl termini must be activated. A variety of activation agents can be used, but should preferably not promote the formation of an oxazolone. An anhydride compound that is sterically hindered might be appropriate. In an alternative embodiment the activated terminal carboxyl can be reacted with a solid phase support functionalised with an appropriate group to react with the activated carboxyl. A free amine group would be appropriate. To permit selective release the carboxyl reactive functionality should be linked to the support by a cleavable linker. A variety of cleavable linkers are known in the art. Photocleavable linkers are well known in the art (Lloyd-Williams et at., Tetrahedron 49:11065–11133, 1993). There are also numerous chemically cleavable linkers, e.g. thioesters may be cleaved by hydroxyl-armine.

In step 8 of the first and second preferred aspects of this invention the C-terminally modified proteins are then treated with a sequence specific cleavage agent. Preferred cleavage agents are chemical reagents which are volatile permitting easy removal of unreacted reagent. Appropriate chemical cleavage reagents include cyanogen bromide which cleaves at methionine residues and BNPS-skatole which cleaves at tryptophan residues (D. L. Crimmins et al., Anal. Biochem. 187:27–38, 1990). In other embodiments sequence specific endoproteinases such as trypsin, chymotrypsin, thrombin or other enzymes may be used.

In step 9 of the first and second preferred aspects of this invention the terminally modified peptides are captured on a solid phase support. In embodiments where the terminal carboxyl is biotinylated the C-terminal peptides may then be captured onto a solid phase support derivitised with streptavidin. The non-terminal peptides can then be washed away.

In step 10 of the first and second preferred aspects of this invention the captured C-terminal peptides are optionally reacted with a mass spectrometry sensitisation reagent. The ion detectors of a mass spectrometer are extremely sensitive, and can detect the arrival of single ions. Thus detection of ions is not the limiting factor that determines the sensitivity of a mass spectrometer. Generally, the most limiting factor is the ionisation of the analyte. In a typical electrospray source or FAB source, only one in a thousand molecules of analyte will actually ionise and be detected. For the purposes of improving this process, it is desirable to introduce a sensitisation compound into the peptides for detection that will pre-ionise the peptide. Preferred compounds include quaternary ammonium ions or metal ion chelation agents. An exemplary compound might be 4-(3-pyridylmethylaminocarboxypropyl)phenyl isocyanate (E. J. Bures et al., "Synthesis and evaluation of a panel of novel reagents for stepwise degradation of polypeptides", Methods in Protein Structure Analysis, Plenum Press, New York, 1995 disclose the use of the isothiocyanate form of this compound as a mass spectrometry sensitiser). The introduction of a sensitisation group not only improves sensitivity but also reduces the risk of competition for ionisation by analyte molecules. This means that all peptides should be more evenly represented in the mass spectrum.

In step 11 of the first and second preferred aspects of this invention the captured C-terminal peptides are then released from the solid phase support. In embodiments where the terminal carboxyl is biotinylated, the avidin captured peptides can be released by treatment with acid. Preferably TFA is used to facilitate recovery of the released peptides as this is volatile and can be readily evaporated to permit recovery of the peptides.

In step 12 of the first and second preferred aspects of this invention he released peptides are recovered. In step 13 of the third and fourth aspects of this invention the peptides are analysed by mass spectrometry. In one embodiment the peptides are embedded in a MALDI matrix, such as cinammic acid, on an appropriate support and are analysed by MALDI mass spectrometry to determine a peptide mass fingerprint for the population of C-terminal peptides. MALDI is a preferred analysis technique as this ionisation technique favours the formation of [M+H]+ions. Thus there is usually only one major peak in the mass spectrum for each peptide.

In a further embodiment the recovered peptides may be dissolved in an appropriate solvent and can be analysed by a spraying inlet system such as electrospray ionisation mass spectrometry. Similarly Fast Atom Bombardment (FAB) and related interfaces may be used. This may include in-line liquid chromatography separation of peptides prior to analysis by mass spectrometry. Capillary electrophoresis may be used, or HPLC or capillary iso-electric focusing. Dynamic FAB is a particularly preferred method as this method of ionisation promotes the generation of ions in the form in which they exist in the matrix used to introduce them into the mass spectrometer. This means that the ions present in the mass spectrum ought to be the same as they are in solution if a liquid matrix is used. Since in the present invention reactive side chains may be capped and a mass spectrometry sensitisation agent may be introduced into the peptides to be analysed, it is possible to ensure that all peptides have only a single charge in solution which is represented as a single mass peak in the final mass spectrum of a peptide population. Tandem mass spectrometers can be coupled to a spraying interface or to a FAB interface. Tandem mass spectrometry permits sequence information to be determined for a peptide and permits identification of covalent modifications of the protein.

The use of DITC glass

Various embodiments of the third preferred aspect of this invention are discussed here.

In step 1 of the third preferred aspect of this invention a population of proteins is completely digested with a Lys-C specific cleavage enzyme, e.g. endoproteinase Lys-C from Lysobacter enzymogenes (Boehringer Mannheim).

In step 2 of the third preferred aspect of this invention the resultant peptide are contacted with a solid support which reacts with amine. In one embodiment the peptide population is reacted with Isothiocyanato glass (DITC glass, Sigma) in the presence of a base. This captures all peptides to the support through any free amino groups.

In step 3 of the third preferred aspect of this invention the captured peptides are contacted with a reagent that which cleaves at the alpha amino groups of each peptide on the support. In embodiments where DITC glass is used the peptides are treated with an appropriate volatile acid (TFA) which cleaves the N-terminal amino acid from each peptide on the support. All peptides that are not C-terminal will have a lysine residue covalently linking them to the solid support. Thus free C-terminal peptides are selectively released.

In step 4 of the third preferred aspect of this invention the released peptides can be recovered from the TFA by evaporating the TFA solvent used to cleave the peptides from the support.

In step 5 of the third preferred aspect of this invention the released peptides may be contacted with reagents to cap reactive side chains. Appropriate reagents include those discussed above.

In step 6 of the third preferred aspect of this invention the peptides are optionally reacted with a mass spectrometry sensitisation reagent. See the discussion above regarding step 10 of the first and second preferred aspects of this invention.

In step 7 of the third preferred aspect of this invention the peptides are analysed by mass spectrometry. In one embodiment the terminal peptides are embedded in a MALDI matrix such as cinammic acid and are analysed by MALDI mass spectrometry to determine a peptide mass fingerprint for the population of C-terminal peptides.

As in the other preferred aspects of this invention, alternative methods of analysing peptides by mass spectrometry can be used. Thus in alternative embodiments the recovered peptides may be dissolved in an appropriate solvent and can be analysed by a spraying inlet system such as electrospray ionisation mass spectrometry. Similarly Fast Atom Bombardment and related interfaces may be used. This may also include in-line liquid chromatography separation prior to mass spectrometry. Tandem mass spectrometers can be coupled to a spraying interface or to a FAB interface. Tandem mass spectrometry permits sequence information to be determined for a peptide and permits identification of covalent modifications of the protein.

EXAMPLES

A series of short computer programs (written in PERL) were employed to analyse the SWISSPROT public domain database of protein sequences to determine, for a given organism, what proportion of proteins could be identified uniquely on the basis of their terminal peptide masses alone. Proteins were extracted from the SWISSPROT database release 35. Analyses were performed on data from the H. influenzae genome. The genome of this organism has been completely sequenced and nearly all predicted open reading frames have been identified. There were 1882 H. influenzae proteins present in this release of the database. Profiles with cleavage at methionine by Cyanogen Bromide and cleavage at tryptophan were tested. It was assumed that the terminal amino acid is not cleaved by the profiling chemistry.

In all of the examples it has been assumed that the mass spectrometer has a mass resolution of 5000. This means that the instrument can resolve a difference in mass of 1 part in 5000, or in other words a molecule of mass 5000 daltons can be resolved from a molecule of mass 4999 daltons. It is also assumed that each peptide only gives rise to a single molecular ion peak.

Example 1

Cleavage with Lys-C and SCN

In this example the 1882H. influenzae proteins are cleaved with the endoproteinase Lys-C which cuts proteins at the C-terminal side of a Lysine residue. The peptides are then reacted with a solid phase support derivitised with phenylisothiocyanate moieties which readily react with primary amines generated at the cleavage sites and present on Lysine side chains as described above. All peptides have at least 1 lysine residue except the C-terminal peptide which has none. All peptides are captured onto the solid support by their N-terminal primary amines. All non C-terminal peptides are also captured by their lysine side chains as well. Phenylisocyanate can be induced to cleave the N-terminal residue of all peptides. All lysine residue carrying peptides will still remain attached to the support as these isothiocyanate derivatives cannot cleave. Thus C-terminal peptides are released from the solid phase support. The C-terminal peptides can then be isolated. They may be modified further if desired for reasons discussed above. After isolation of the C-terminal peptides and any additional side chain modifications the peptides may be analysed by mass spectrometry.

It is assumed that no other side chains are capped and the unmodified peptides are analysed directly.

Results 1882 protein records analysed.
7 proteins did not have a cleavage site for the reagent used.
870 peptide mass(es) shared by 1 protein(s)
155 peptide mass(es) shared by 2 protein(s)
43 peptide mass(es) shared by 3 protein(s)
19 peptide mass(es) shared by 4 protein(s)
6 peptide mass(es) shared by 5 protein(s)
9 peptide mass(es) shared by 6 protein(s)
2 peptide mass(es) shared by 7 protein(s)
3 peptide mass(es) shared by 8 protein(s)
1 peptide mass(es) shared by 9 protein(s)
1 peptide mass(es) shared by 10 protein(s)
2 peptide mass(es) shared by 11 protein(s)
2 peptide mass(es) shared by 12 protein(s)
1 peptide mass(es) shared by 13 protein(s)
1 peptide mass(es) shared by 17 protein(s)
1 peptide mass(es) shared by 19 protein(s)
1 peptide mass(es) shared by 23 protein(s)
1 peptide mass(es) shared by 33 protein(s)
1 peptide mass(es) shared by 205 protein(s)

This peptide mass fingerprint identifies 46.2% of proteins uniquely on the basis of their terminal peptide mass alone.

Example 2

Capping hydroxy side-chains

In this example the reactive hydroxyl carrying side chains of serine, threonine and tyrosine are capped with a silyl protecting group generating for example trimethylsilyl derivatives at these side chains. The side chain carboxyl groups are activated with an appropriate reagent, such as tetraphenylpyrophosphate and these are then converted to piperidine amides by reaction with piperidine in the presence of a base as described above.

Results 1882 protein records analysed.
7 proteins did not have a cleavage site for the reagent used.
937 peptide mass(es) shared by 1 protein(s)
149 peptide mass(es) shared by 2 protein(s)
34 peptide mass(es) shared by 3 protein(s)
17 peptide mass(es) shared by 4 protein(s)
6 peptide mass(es) shared by 5 protein(s)
8 peptide mass(es) shared by 6 protein(s)
2 peptide mass(es) shared by 7 protein(s)
4 peptide mass(es) shared by 8 protein(s)
2 peptide mass(es) shared by 10 protein(s)
1 peptide mass(es) shared by 11 protein(s)
1 peptide mass(es) shared by 12 protein(s)
1 peptide mass(es) shared by 13 protein(s)
1 peptide mass(es) shared by 17 protein(s)
1 peptide mass(es) shared by 19 protein(s)
1 peptide mass(es) shared by 23 protein(s)
1 peptide mass(es) shared by 33 protein(s)
1 peptide mass(es) shared by 205 protein(s)

This peptide mass fingerprint identifies 49.8% of proteins uniquely on the basis of their terminal peptide mass alone.

Example 3

C-terminal capture and cleavage with cyanogen bromide

In this example the 1882H. influenzae proteins are immobilised non-covalently onto a solid phase support. The proteins are treated with trifluoroacetic anhydride. This reagent will cap the reactive side chains of lysine, serine, threonine and tyrosine to give trifluoroacetyl derivatives. This reagent will also activate side chain and terminal carboxyl groups. The C-terminal activated carboxyls spontaneously form an oxazolone. The unreacted trifluoroacetic anhydride is washed away. The activated side chains are then reacted with piperidine in the presence of a non-aqueous base which will generate piperidine amides at the activated side chain carboxyls. The C-terminal oxazolone is then hydrolysed back to the original free carboxyl which is then modified to permit capture onto a solid phase support, e.g. by biotinylation. The modified proteins are then cleaved with cyanogen bromide which cleaves at methionine residues. The resultant peptides are washed in an inert solvent and released from the solid phase support on which the chemistry is performed. The ° C-terminal peptides are selectively biotinylated permitting them to be captured onto an avidinated support. This allows non-terminal peptides to be washed away. The C-terminal peptides are then released from the solid support and analysed by mass spectrometry.

Results 1882 protein records analysed.
18 proteins did not have a cleavage site for the reagent used.
1461 peptide mass(es) shared by 1 protein(s)
157 peptide mass(es) shared by 2 protein(s)
21 peptide mass(es) shared by 3 protein(s)
4 peptide mass(es) shared by 4 protein(s)
2 peptide mass(es) shared by 5 protein(s)
3 peptide mass(es) shared by 6 protein(s)

This peptide mass fingerprint identifies 77.6% of proteins uniquely on the basis of their terminal peptide mass alone.

Example 4

C-terminal capture and cleavage with BNPS-skatole

In this example the 1882H. influenzae proteins are treated as in example 3 except that after the C-terminal carboxyl has been modified to permit capture onto a solid phase support the proteins are cleaved with BNPS-skatole (3-bromo-3-methyl-2-(o-nitrophenylsulphenyl)indolenine) which cleaves proteins chemically at tryptophan residues rather than cyanogen bromide. The resultant peptides are then desorbed from their solid phase support and incubated with an avidinated support. This allows non-terminal peptides to be washed away. The C-terminal peptides are then released from the solid support and analysed by mass spectrometry. In this example, therefore, the reactive side chains of lysine, serine, threonine and tyrosine are trifluoroacetyl derivatives again and side chain carboxyls are piperidine amide derivatives.

Results 1882 protein records analysed.
361 proteins did not have a cleavage site for the reagent used.
1484 peptide mass(es) shared by 1 protein(s)
163 peptide mass(es) shared by 2 protein(s)
15 peptide mass(es) shared by 3 protein(s)
5 peptide mass(es) shared by 4 protein(s)
1 peptide mass(es) shared by 7 protein(s)

This peptide mass fingerprint identifies 78.9% of proteins uniquely on the basis of their terminal peptide mass alone.

Example 5

Combining two profiles

The list of unique proteins generated in example 3 where cleavage Cyanogen Bromide was used and in the example 4 where cleavage by BNPS-skatole was used were combined to determine the sum of proteins that were identified uniquely on the basis of their mass alone between the two profiles.

1774 proteins are uniquely resolved between the two profiles. This amounts to resolving 94.3% of the H. influenzae proteins in the SWISSPROT database uniquely on the basis of terminal peptide masses alone. This is a 19.5% improvement in resolution over the better individual profile.

What is claimed is:

1. A method for characterising a populatin of parent polypeptides in a sample, which method comprises:

(a) contacting a first portion of the sample with a first sequence-specific cleavage agent to generate polypeptide fragments;

(b) isolating one or more polypeptide fragments, each fragment comprising the N-terminus or the C-terminus of the parent polypeptide from which it was fragmented;

(c) identifying the isolated fragments by mass spectrometry;

(d) repeating steps (a)–(c) on a second portion of the sample using a second sequence-specific cleavage agent that cleaves at a different site from the first cleavage agent, wherein the second cleavage agent is different from the first cleavage agent, and wherein the second portion of the sample is separate from the first portion of the sample; and (e) characterising the parent polypeptides in the sample from the fragments identified in steps (c) and (d).

2. A method according to claim 1, wherein the step (d) comprises repeating steps (a)–(c) two or more times, each time using a portion of sample which is separate from the previous portions, and each time using a further cleavage agent that cleaves at a different site from the previous cleavage agents.

3. A method according to claim 1 or claim 2, comprising a further capping step prior to step (a), which capping step comprises reacting the parent polypeptides in the portion of sample with one or more capping agents to introduce capping groups on one or more reactive side chains of the polypeptides.

4. A method according to claim 3, wherein the capping step and steps (a)–(c) are repeated one, two, or more times, each time using a portion of sample which is separate from the previous portions, and each time introducing capping groups at the same side chains as the previous capping steps, but using capping groups having different mass than the corresponding capping groups used in the previous capping steps.

5. A method for characterising a parent polypeptide or a population of parent polypeptides in the sample, which method comprises:
(f) contacting a first portion of the sample comprising one or more polypeptides with a first capping agent in a first capping step to introduce capping groups on one or more reactive side chains of the polypeptides;
(g) contacting the first sample with a sequence-specific cleavage agent to generate polypeptide fragments;
(h) isolating one or more polypeptide fragments, each fragment comprising the N-terminus or the C-terminus of the parent polypeptide from which it was fragmented;
(j) identifying the isolated fragments by mass spectrometry;
(k) repeating steps (f)–(j) on a second portion of the sample using a second capping groups that introduces capping groups at the same side chains as the first capping step, but uses capping groups having different mass than the capping groups used in the first capping step, wherein the second portion is separate from the first portion; and
(l) characterising the one or more parent polypeptides in the sample from the fragments identified in steps (j) and (k).

6. A method according to claim 5, wherein the steps (f)–(i) are repeated two or more times, each time using a portion of sample which is separate from the previous portions, and each time introducing capping groups at the same side chains as the previous capping steps, but using capping groups having different mass than the corresponding capping groups used in the previous capping steps.

7. A method according to claim 5 or claim 6, wherein the step (k) comprises repeating steps (f)–(j) one, two, or more times, each time using a portion of sample which is separate from tho previous portions, and each time using a further cleavage agent that cleaves at a different site from the previous cleavage agents.

8. A method according to claim 5, wherein the side chains to be capped comprise one or more of the following:
the $NH_2$ side chain in arginine;
the $NH_2$ side chain in asparagine;
the $NH_2$ side chain in glutamine;
the $N_2$ side chain in lysine;
the COOH side chain in aspartic acid;
the COOH side chain in glutamic acid;
the OH side chain in serine;
the OH side chain in threonine;
the OH side chain in thyroxine;
the OH side chain in tyrosine; and
the SH side chain in cysteine.

9. A method according to claim 1, wherein the fragments are isolated by capture on a solid phase, such as isothiocyanato glass (or DITC glass) or polystyrene isothiocyanate.

10. A method according to claim 9, wherein the capture involves covalently bonding the fragments to the solid phase.

11. A method according to claim 10, wherein the fragments are bound to the solid phase through their N-termini.

12. A method according to claim 1, wherein each isolated fragment comprises the C-terminus of the parent polypeptide from which it was fragmented.

13. A method according to claim 1, wherein the cleavage agent employed comprises an endopeptidase or a chemical cleavage agent.

14. The method of claim 13, wherein the cleavage agent is at least one compound selected from the group consisting of a Lys-C endopeptidase, a thiocyanate compound, cyanogen bromide, 3-bromo-3-methyl-2(o-nitrophenyl sulphenyl) indolenine-skatole, trypsin, chymotrypsin and/or thrombin.

15. The method of claim 5 therein the capping agent is at least one compound selected from the group consisting of an iodacetate compound, an isocyanate compound, a silyl compound, an anhydride, a vinylsulphone compound and a vinyl pyridine derivative.

16. The method of claim 1 which method further comprises characterizing the one or more parent polypeptides in the sample by comparison with a database based on terminal peptide mass.

17. A method for detecting the expression of one or more proteins in a tissue, which method comprises characterizing a population of parent polypeptides in a sample of tissue comprising the following steps:
(a) contacting a first portion of the sample comprising one or more parent polypeptides with a first sequence-specific cleavage agent to generate polypeptide fragments;
(b) isolating one or more polypeptide fragments, each fragment comprising the N-terminus or the C-terminus of the parent polypeptide from which it was fragmented;
(c) identifying the isolated fragments by mass spectrometry;
(d) repeating steps (a)–(c) on a second portion of the sample using a second sequence-specific cleavage agent that cleaves at a different site from the first cleavage agent, wherein the second cleavage agent is different from the first cleavage agent, and wherein the second portion of the sample is separate from the first portion of the sample; and
(e) characterizing the one or more parent polypeptides in the sample from the fragments identified in steps (c) and (d).

18. The method of claim 17 which further comprise chracterizing the population of parent polypeptide by comparison with a database based on terminal peptide mass.

19. A method for assaying for one or more specific polypeptides in a sample, which method comprises characterizing a population of parent polypeptides comprising the following steps:
(a) contacting a first portion of the sample comprising one or more parent polypeptides with a first sequence-specific cleavage agent to generate polypeptide fragments;
(b) isolating ore or more polypeptide fragments, each fragment comprising the N-terminus or the C-terminus of the parent polypeptide from which it was fragmented;

(c) identifying the isolated fragments by mass spectrometry;

(d) repeating steps (a)–(c) on a second portion of the sample using a second sequence-specific cleavage agent that cleaves at a different site from the first cleavage agent, wherein the second cleavage agent is different from the first cleavage agent, and wherein the second portion of the sample is separate from the first portion of sample; and (e) characterizing the one or more parent polypeptides in the sample from the fragments identified in steps (c) and (d); and (f) determining the presence or absence of said one or more specific polypeptides based on the presence or absence of one or more specific fragments corresponding to said polypeptides.

20. The method of claim 19, which further comprises characterizing said population of parent polypeptides by determining the presence or absence of said one or more specific polypeptides by comparison to a database based on terminal peptide mass.

* * * * *